US006991815B2

(12) United States Patent
Ko et al.

(10) Patent No.: US 6,991,815 B2
(45) Date of Patent: Jan. 31, 2006

(54) ANTI-ULCER PHARMACEUTICAL COMPOSITION AND THE PREPARATION THEREOF

(75) Inventors: Feng-Nien Ko, Taipei (TW); Chien-Jen Shih, Taipei (TW); Je-Yie Lin, Taipei Hsien (TW); Pey-Chyi Wu, Taipei (TW); Mo-Chi Cheng, Taipei (TW)

(73) Assignee: Medical and Pharmaceutical Industry Technology and Development Center, Taipei Hsien (TW)

( * ) Notice: Subject to any disclaimer, the term of this patent is extended or adjusted under 35 U.S.C. 154(b) by 0 days.

(21) Appl. No.: 10/850,217

(22) Filed: May 20, 2004

(65) Prior Publication Data

US 2004/0213860 A1    Oct. 28, 2004

Related U.S. Application Data

(62) Division of application No. 09/522,434, filed on Mar. 9, 2000.

(30) Foreign Application Priority Data

Jan. 11, 2000    (TW)    ............................... 89100334 A

(51) Int. Cl.
*A61K 35/78*    (2006.01)
(52) U.S. Cl. .................................................... 424/728
(58) Field of Classification Search ................ 424/728
See application file for complete search history.

(56) References Cited

U.S. PATENT DOCUMENTS 4,795,742 A    1/1989    Liu 5,459,041 A    10/1995    Blaser et al.

FOREIGN PATENT DOCUMENTS

| DE | 3609005 A1 | 3/1986 |
| DE | 3328262 C2 | 1/1998 |
| GB | 2 364 640 A | 2/2002 |
| JP | 53-91109 | 10/1989 |
| WO | WO 99/30725 A1 | 6/1999 |

OTHER PUBLICATIONS

CAPLUS English abstract of JP 62005126 B4 (Feb. 1987).
Denwent English abstract of CN 1079655 A (Dec. 1993).
Denwent English abstract of CN 1134832 A (Nov. 1996).
M. W. Chang. "Effect of ginseng extracts on production of vacuolating toxin by *Helicobacter pylori*". Taehan Misaengmul Hakhoechi 32(5):539-551, 1997. CAPLUS 1997:778804.
Database WPI, Section Ch, Week 199246. Derwent Publications Ltd., London GB; AN 1992-375618. XP002245679 & JP 04 273824 A (Nitto Denko Corp), Sep. 30, 1992.
Database WPI, Section Ch, Week 197948. Derwent Publications Ltd., London GB; AN 1979-86683B. XP002245677 & JP 54-135210 A (Arichi S), Oct. 20, 1979.

*Primary Examiner*—Susan D. Coe
(74) *Attorney, Agent, or Firm*—Fish & Richardson P.C.

(57) ABSTRACT

The invention discloses a pharmaceutical composition for preventing and/or treating peptic ulcer, including American ginseng or the extract thereof, and a method for preparing American ginseng extract, said method including extracting American ginseng with water or ethanol aqueous solution, and then ultrafiltrating, dialyzing, precipitating with ethanol, or performing reverse phase chromatography to obtain various fractions of extract with anti-peptic ulcer effect.

10 Claims, No Drawings

ANTI-ULCER PHARMACEUTICAL COMPOSITION AND THE PREPARATION THEREOF

RELATED APPLICATIONS

This application is a divisional application and claims priority to U.S. application Ser. No. 09/522,434, filed Mar. 9, 2000, the contents of which are incorporated herein in their entirety.

BACKGROUND OF THE INVENTION

1. Field of the Invention

The present invention relates to pharmaceutical compositions useful for the prevention and/or treatment of peptic ulcer diseases. More particularly, it relates to the use of American ginseng or the extract thereof as the active ingredient for the prevention and treatment of peptic ulcer diseases.

2. Description of the Related Arts

American ginseng (Panax quinquefolium L.) is one species of Araliaceae, which is the North American variety of ginseng native to the United States and Canada. The Panax plants in Araliaceae, such as Panax ginseng, Panax quinquefolium, Panax pseudo-ginseng etc, have been used as a form of tonic medicine in Chinese for a long period of time, and Panax ginseng is traditionally considered a valuable medicinal material in China, Japan and Korea. After harvesting, Panax ginseng with good quality is generally treated with boiling water or steam to give red ginseng. Panax ginseng which has been dried by hot air or sunlight is called white ginseng or unprocessed ginseng. The American ginseng is an herbaceous perennial and its root is mainly used as a nutritious tonic agent. Its morphology is similar to Panax ginseng, but has less fiber-like or lateral roots. At present, the American ginseng is artificially cultivated in the United States, Mainland China and Russia. Many reports have shown some components of American ginseng are similar to Panax ginseng, including several kinds of ginseng saponins, oligosaccharides, volatile oils, amino acids, vitamins and trace elements. It is traditionally believed that both American ginseng and Panax ginseng possess effects of increasing physical strength, nourishing and preserving health, and prolonging life. Thus, they are regarded as mild tonics used for daily dietary or medicinal remedy.

Recently, a number of scientific reports show that the American ginseng indeed possesses a variety of physiological or pharmaceutical activities, including anti-aging (Xiao P. G. et. al., 1993, Journal of Ethnopharmacology 38(2–3): 167–75); preventing atherosclerosis and hyperlipidemia (Li J. et. al., 1999, Life Science 64(1):53–62); protecting liver from injury (Yoshikawa M. et. al., 1998, Chemical and Pharmaceutical Bulletin 46(4) :647–54); enhancing the function of cardiovascular system (Kwan C. Y., 1995, Clinical and Experimental Pharmacology and Physiology-Supplement 1:S297–9; Yang S., 1992, China Journal of Chinese Material Medica 17(9):555–7 and U.S. Pat. No. 4,708,949); preventing memory dysfunction and dementia (Benishin C. G., 1991, Pharmacology 42(4):223–9; Li Z. et. al., 1999, Journal of Pharmacy and Pharmacology 51(4) :435–40; Lewis R. et. al., 1999, Phytotherapy Research 13(1) :59–64); decreasing hyperglycemia (Oshima Y. et. al., 1987, Journal of Natural Products 50(2) :188–90; Martinez S. and Staba E. J., 1984, Japanese Journal of Pharmacology 35 (2) :79–85); inhibition of breast cancer cells (Duda R. B. et. al., 1996, Annals of Surgical Oncology 3(6) :515–20); enhancing physical strength; antiviral activity (U.S. Pat. No. 5,071,839); anti-oxidation; decreasing the side effects of anticancer chemotherapy and radiotherapy (U.S. Pat. No. 4,945,115); modulating gastric digestion (Yuan C. S. et. al., 1998, American Journal of Chinese Medicine 26(1) :47–55); and increasing the immune function (U.S. Pat. No. 4,795, 742) etc.

Recently, the population with gastrointestinal diseases has been increasing, especially in highly developmental countries. The causes of peptic ulcers include unrelieved daily pressure; excessive alcohol irritation; the side effects of drugs, such as aspirin or non-steroid anti-inflammatory drugs; or Helicobacter pyroli infection. The predominant drugs used to treat peptic ulcers include muscarinic antagonists, such as methscopolamine bromide; $H_2$ blockers, such as cimetidine; antacids, such as aluminum hydroxide or magnesium hydroxide; $H^+/K^+$ ATPase inhibitor, such as omeprazole; anti-bacterial drugs, such as admixture of amoxicillin and metronidazole. Such drugs may be classified into two categories: one is used for physical protection of gastric mucosa to mitigate the irritation of the gastric acid to the mucosa ulcer site; the other is used for chemically inhibiting the secretion of the gastric acid, to avoid ulceration produced from excessive gastric acid erosion. The prevalence of peptic ulcers and their high rate of recurrence may due to patients' life style or season change and many patients repeatedly suffer from peptic ulcers. Thus, there is a need for a safe, mild and effective drug for treating and preventing peptic ulcers.

SUMMARY OF THE INVENTION

It is an object of the present invention to provide pharmaceutical compositions which are effective in preventing and/or treating peptic ulcer diseases, comprising an effective amount of American ginsengand/or the extract thereof, and a physiologically or pharmaceutically acceptable carrier.

An additional object of the present invention is to provide a process of preparing the extracts of the American ginseng described above, comprising the steps of (a) extracting American ginsengwith a solvent with a polarity higher than 0.88 to obtain an extract; (b) filtering the extract to obtain a filtrate; and (c) centrifuging the filtrate to obtain a supernatant (total extract).

The preparation process according to the present invention may further comprise the means of ultrafiltrating, dialyzing, precipitating with ethanol, or performing reverse phase chromatography, to obtain certain fractions of American ginsengextract.

Another object of the present invention is to provide methods for preventing and/or treating a patient suffering from peptic ulcer, comprising administrating an effective amount of American ginsengand/or the extracts thereof to said patient.

DETAILED DESCRIPTION OF THE INVENTION

In accordance with the present invention, there is provided a process of preparing the pharmaceutical compositions comprising American ginsengor the extract thereof. First, American ginsengis extracted with a solvent with a polarity higher than 0.88 to obtain an extract. Suitable solvent includes water, ethanol, methanol or the mixtures thereof, preferably water or ethanol, and more preferably 10%~80% ethanol aqueous solution. Next, the extract is filtered to remove plant residues, and then centrifuged to remove microparticles and impurities. The resulting supernatant (total extract) is concentrated into an appropriate concentration, and then further treated by one or more of the following processes: ultrafiltrating, dialyzing, precipitating with ethanol, or performing reverse phase chromatography, to obtain various fractions of American ginsengextract.

In the process described above, ultrafiltrating is a step which the total extract is filtered by the ultrafiltration membrane with molecular weight cut off 1,000 or 3,000 to give a retentate and a filtrate. Dialyzing is a step in which the total extract is dialyzed by a membrane or dialysis bag with molecular weight cut off 500 to remove smaller molecules. Precipitating with ethanol is a step in which the filtrate obtained from ultrafiltration is concentrated to dry and then dissolved with 50%~100% ethanol to obtain the soluble portion. Performing reverse phase chromatography is a step in which the filtrate obtained from ultrafiltration is loaded onto a reverse phase polyaromatic resin column, such as Diaion HP-20 (Sigma, Cat. No. I-3605), to elute the active fraction of American ginsengextract.

All American ginsengextracts obtained from various processes of the present invention possess an anti-peptic ulcer effect. Moreover, these extracts may be added a physiologically acceptable carrier and/or formulated with a pharmaceutically acceptable excipient to obtain a pharmaceutical composition which is effective in treating or preventing peptic ulcers. The term "peptic ulcer" used hereinbefore and hereinafter refers to gastric ulcers and/or duodenal ulcers.

Without intending to limit it in any manner, the present invention will be further illustrated by the following examples which are associated with the design of the extraction step(s) and the assessment of pharmacological activity.

EXAMPLE 1

2,000 ml of deionized water was added to 200 g of chopped American ginsengand then heated to boil and further refluxed for 1 hour. The decoction was filtered through sieve gauge No. 200 (sieve pore 0.074 mm), and the filtrate (first filtrate) was collected. An additional 2,000 ml of deionized water was added to the residue of the American ginsengdescribed above, and was refluxed and filtered as described above to give the second filtrate. These two filtrates were combined and centrifuged at 10,000 rpm for 30 minutes to remove microparticles and impurities. The supernatant (total extract) was then filtered through the ultrafiltration membrane with molecular weight cut off 1,000 (Amicon, Cat. No. S1Y1) to remove substances with molecular weight less than 1,000 dalton. The retentate containing substances with molecular weight greater than 1,000 dalton was concentrated under reduced pressure to give the extract I. The filtrate containing substances with molecular weight less than 1,000 dalton was concentrated to dry, and then 90% ethanol solution was added to dissolve those substances. The ethanol solution was filtered (Advantec No. 2) to obtain the soluble portion, and the resulting soluble portion was added into the extract I described above. The mixture was concentrated under reduced pressure to give the extract II.

EXAMPLE 2

The total extract described in EXAMPLE 1 was treated through an ultrafiltration membrane with molecular weight cut off 3,000 (Amicon, Cat. No. S1Y3) to remove substances with molecular weight less than 3,000 dalton. The retentate containing substances with molecular weight greater than 3,000 dalton was concentrated under reduced pressure to give the extract III. The filtrate containing substances with molecular weight less than 3,000 dalton was loaded onto a column packed with Diaion HP-20 resin (Sigma, Cat. No. I-3605). The column was first eluted with deionized water until the eluate was colorless, and then eluted with 95% ethanol and the eluate was collected. The 95% ethanol eluate was added into the extract III described above. The mixture was concentrated under reduced pressure to give the extract IV.

EXAMPLE 3

The total extract described in EXAMPLE 1 was loaded in a dialysis bag with molecular weight cut off 500 (Spectra/Por®, Cat. No. 131 057). Both ends of the bag were sealed with clamps. The bag was placed in a bucket contained deionized water, in which the ratio of the supernatant and deionized water was 1:10. The total extract was dialyzed at 4° C. with stirring thrice each for 20 hours. The solution remaining in dialysis bag was collected and concentrated under reduced pressure to give the extract.

EXAMPLE 4

1,000 ml of 80% ethanol solution was added to 100 g of chopped American ginsengand was heated to boil and further refluxed for 1 hour. The decoction was filtered through sieve gauge No. 200, and the filtrate (first filtrate) was collected. An additional 1,000 ml of 80% ethanol solution was added to the residue of the ginsengand extracted as described above, to give the second filtrate. These two filtrates were combined and concentrated under reduced pressure to give the extract V.

EXAMPLE 5

Assessment of the Pharmacological Activity of Anti-peptic Ulcer

The anti-peptic ulcer activity of American ginsengwas assessed using the methods described by Robert A. et. al. (1979, *Gastroenterology* 77:433–443), and Takagi I. and Okabe S. (1968, *Japan J. Pharmacol.* 18:9–18), which is summarized below.

(1) The Assessment of Stress-induced Ulcer

Male Long Evans rats, weighing 150±20 g, were administrated American ginsengextracts orally after being fasted for 18 hours, while the control rats were administrated the same volume of distilled water orally. After 1 hour, the rats were placed in a holder and partially immersed in water at 22~24° C. for 4 hours. The rats were then sacrificed and their stomachs were opened along the greater curvature for evaluation the degree of ulceration. Gastric ulceration was scored according to an arbitrary system:

0=no bleeding
1=spot bleeding
2=slight bleeding
3=severe bleeding and half stomach bloodstained
4=very severe bleeding and entire stomach bloodstained

TABLE 1

Effect of American ginseng extracts on stress-induced ulcer in rat.

| Treatment | Dose (g/kg) | N | Inhibition (%)[a] |
|---|---|---|---|
| Total Extract | 4 | 10 | 27.5 ± 2.4 |
| Extract I | 4 | 10 | 42.5 ± 3.6 |
| Extract II | 4 | 6 | 37.5 ± 5.1 |
| Extract III | 4 | 10 | 42.5 ± 3.6 |
| Extract IV | 4 | 6 | 51.2 ± 3.8 |
| Extract V | 4 | 4 | 37.5 ± 6.3 |

[a]The inhibition rate (%) is calculated by the following equation: [(score of control animal) − (score of experimental animal)]/(score of control animal) × 100%.
All the ulcer scores of the control rats were 4.

(2) The Assessment of Ethanol-induced Ulcer:

Male Long Evans rats, weighing 150±20 g, were administrated American ginsengextracts orally after being fasted for 18 hours, while the control rats were administrated the same volume of distilled water orally. After 15 minutes, the rats were administered 1 ml of absolute ethanol. After 1 hour, the rats were sacrificed and gastric ulceration was scored according to an arbitrary system:

0=no lesions
1=hyperaemia
2=one or two slight lesions
3=more than two slight lesions or severe lesions
4=very severe lesions

TABLE 2

Effect of American ginseng extract on ethanol-induced ulcer in rat.

| Treatment | Dose (g/kg) | N | Inhibition (%)[a] |
|---|---|---|---|
| Total Extract | 4 | 10 | 50.0 ± 0.0 |
| Extract I | 4 | 10 | 50.0 ± 0.0 |
| Extract II | 4 | 6 | 45.8 ± 3.8 |
| Extract III | 4 | 10 | 40.0 ± 5.2 |

[a]The inhibition rate (%) is calculated by the following equation: [(score of control animal) − (score of experimental animal)]/(score of control animal) × 100%.
All the ulcer scores of the control rats were 4.

The results of pharmacological assessment shown in Tables 1 and 2 reveal that American ginsengextracts of the present invention possess excellent inhibition effects of gastric ulcers induced by stress and alcohol. In addition, according to the present invention, the American ginseng extracted with water or ethanol solution and further treated by ultrafiltration, dialysis, precipitation with ethanol, or reverse phase chromatography, possesses excellent anti-peptic ulcer effects.

While the invention has been particularly shown and described with the reference to the preferred embodiment thereof, it will be understood by those skilled in the art that various changes in form and details may be made without departing from the spirit and scope of the invention.

What is claimed is:

1. A method for preventing and/or treating a patient suffering from peptic ulcer, comprising administering an effective amount of an American ginseng extract to said patient, wherein the American ginseng extract is obtained by:

extracting American ginseng with a solvent having a polarity higher than 0.88 to obtain an extract;
filtering said extract to obtain a filtrate;
centrifuging said filtrate and collecting a supernatant; and
separating said supernatant with a molecular weight cut-off of at least 1,000 to give a fraction with molecular weight of greater than 1,000, and said fraction being concentrated to give said American ginseng extract,
wherein the American ginseng extract contains compounds with molecular weights of at least 3,000.

2. The method as claimed in claim 1, wherein the solvent is water or a 10%~80% aqueous ethanol solution.

3. The method as claimed in claim 1, wherein the separating step is conducted by an ultrafiltration membrane having a molecular weight cut-off of 1,000.

4. The method as claimed in claim 1, wherein the separating step is conducted by an ultrafiltration membrane having a molecular weight cut-off of 3,000.

5. The method as claimed in claim 1, wherein the solvent is a 10%~8% aqueous ethanol solution; and the American ginseng extract further comprises a composition obtained by separating said supernatant with a molecular weight cut-off of at least 1,000 to give a solution containing substances having molecular weights of less than 1,000 dalton, the solution being concentrated to dry and mixed with an ethanol solution to dissolve said substances, and filtering said ethanol solution to obtain a soluble portion as a part of said American ginseng extract.

6. The method as claimed in claim 1, wherein the solvent is a 10%~80% aqueous ethanol solution; the separating step is conducted by an ultrafiltration membrane with a molecular weight cut-off of 3,000; and the American ginseng extract further comprises a composition obtained by separating said supernatant with a molecular weight cut-off of 3,000 to give a solution containing substances having molecular weights of less than 3,000 dalton, loading the solution onto a reverse phase column, eluting the column with water and a 95% ethanol solution, and collecting a 95% ethanol eluate as a part of said American ginseng extract.

7. A method for preventing and/or treating a patient suffering from peptic ulcer, comprising administrating an effective amount of American ginseng extract to said patient, wherein the American ginseng extract is obtained by:

extracting American ginseng with a solvent with a polarity higher than 0.88 to obtain an extract;
filtering said extract to obtain a filtrate;
centrifuging said filtrate and collecting a supernatant; and
separating said supernatant with molecular weight cut off at least 3,000 to give a fraction with molecular weight greater than 3,000, and said fraction being concentrated to give said American ginseng extract.

8. The method as claimed in claim 7, wherein the solvent is water or 10%–80% aqueous ethanol solution.

9. The method as claimed in claim 7, wherein separating said supernatant with molecular weight cut off at least 3,000 is using an ultrafiltration membrane with molecular weight cut off 3,000.

10. The method as claimed in claim 7, wherein the solvent is 10%–80% aqueous ethanol solution, separating said supernatant with molecular weight cut off at least 3,000 is using an ultrafiltration membrane with molecular weight cut off 3,000 and the American ginseng extract further comprises a composition obtained by separating said supernatant with molecular weight cut 3,000 to give a filtrate containing substances with molecular weight less than 3,000 dalton, the filtrate being loaded onto a reverse phase column, eluted with water, followed by 95% ethanol solution and collected the 95% ethanol eluate as a part of said American ginseng extract.

* * * * *